(12) United States Patent
Nestler et al.

(10) Patent No.: US 6,252,066 B1
(45) Date of Patent: *Jun. 26, 2001

(54) QUARTERNARY POLYCYCLIC POLYAMMONIUM SALTS AND PROCESS FOR THEIR PREPARATION

(76) Inventors: Bernd Nestler; Michael Seebach, both of Clariant GmbH Patente, Marken, Lizenzen Geb. K 801, D-65926 Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/262,092

(22) Filed: Mar. 4, 1999

(30) Foreign Application Priority Data

Mar. 5, 1998 (DE) ............................................. 198 09 542

(51) Int. Cl.⁷ ..................... C07D 235/02; C07D 243/06; C07D 245/04; C07D 241/36
(52) U.S. Cl. ........................................... 540/472; 544/343
(58) Field of Search .............................. 544/343; 540/472

(56) References Cited

FOREIGN PATENT DOCUMENTS

97/01360 * 1/1997 (WO) .

OTHER PUBLICATIONS

Tadashi Okawara et al ; Heterocycles, vol. 41, No. 5, Jan. 9, 1995.*
G. Weisman et al., "Cross–Bridged Cyclam. Protonation and Li⁺Complexation in a Diamond–Lattice Cleft", J. Am. Chem. Soc. 112 (1990), 8604–8605.
T. Okawara et al., "Preparation and Stereochemistry of 1,4,8,11–Tetraazaperhydropyrene Derivatives From N,N'–Bis(3–Aminopropyl) Ethylenediamine", Heterocycles, vol. 41, No. 5, 1995, 1023–1033.

G. Weisman et al., "Synthesis And Transition–metal Complexes Of New Cross–bridged Tetraamine Ligands", Chem. Commun. 1996, 947–948.

Chem. Communication; Gary R. Weisman et al pp. 947–948, 1996, Dec. 1995.*

* cited by examiner

Primary Examiner—Alan L. Rotman
Assistant Examiner—Rita Desai
(74) Attorney, Agent, or Firm—Susan S. Jackson; Scott E. Hanf

(57) ABSTRACT

Quaternary polycyclic polyammonium salts of the general formula

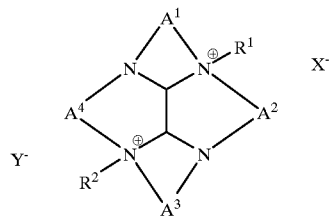

and a process for their preparation are claimed, where $A^1$, $A^2$, $A^3$, $A^4$, $R^1$, $R^2$, X and Y have the meanings mentioned in the description.

13 Claims, No Drawings

QUARTERNARY POLYCYCLIC POLYAMMONIUM SALTS AND PROCESS FOR THEIR PREPARATION

FIELD OF THE INVENTION

This invention relates to specific quaternary polycyclic polyammonium salts having a basic structure of the general formula (1)

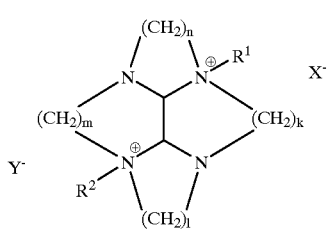

in which k, l, m and n independently of one another are numbers from 2 to 4 and $R^1$ and $R^2$ independently of one another are a substituted or unsubstituted alkyl, cycloalkyl or aryl radical and X and Y are an anion. These compounds serve as starting materials for the preparation of cyclic or bridged polyamine compounds; e.g. for syntheses of pharmacologically active substances, of ligands for catalytically active metal complexes, of host compounds for supramolecular structures and of proton sponges; moreover, these compounds often have unusual redox properties.

DESCRIPTION OF THE RELATED ART

Thus G. Weisman, M. Rogers, E. Wong, J. Jasinksi and E. Paight in J. Am. Chem. Soc. 112 (1990), 8605–8605 describe the preparation of the bridged ligand II by reduction of cis-4,11-dimethyl-4,7,11,14-tetraazaperhydro-pyrenium diiodide (I) by means of sodium borohydride.

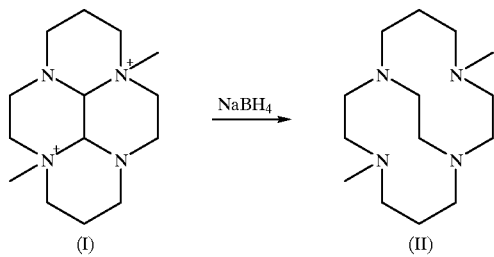

II complexes Li$^+$ ions with unusually high selectivity and proves to be a proton sponge having unusual properties.

In the literature, only a few examples of quaternary polycyclic polyammonium salts having a basic structure of the general formula (1) are known, diiodides and dibromides being described exclusively.

These known diiodides and dibromides, however, are as a rule unsuitable for handling on the industrial scale. In addition to ecological aspects, it is especially disadvantageous that in many reactions (oxidations and reductions) of ammonium salts the presence of halide ions such as iodide or bromide proves to be troublesome; the result is often unsatisfactory yields and the formation of undesirable by-products.

This invention is thus based on the object of finding quaternary polycyclic polyammonium salts having a basic structure of the general formula (1) which can be handled on the industrial scale.

Surprisingly, it has been found that quaternary polycyclic polyammonium salts having a basic structure of the general formula (1) as the methylsulfate or sulfate salt are not afflicted with these disadvantages, and that these compounds can moreover be employed with excellent yield in subsequent reactions, especially reductions with sodium borohydride.

In the literature, only a few methods for the preparation of quatenary polycyclic polyammonium salts having a basic structure of the general formula (1) are described, these were also only worked out for the synthesis of small amounts for scientific purposes.

The reaction of cis-perhydro-3a,5a,8a,10a-tetraazapyrene with 15 equivalents of methyl iodide in acetonitrile was described by G. Weisman, M. Rogers, E. Wong, J. Jasinksi and E. Paight in J. Am. Chem. Soc. 112 (1990), 8604–8605; after a reaction time of 72 hours cis-3a,8a-dimethyl-5a,10a-diaza-3a,8a-diazoniaperhydropyrenium diiodide is obtained here in 80% yield.

In addition to the use of the toxic acetonitrile as a solvent, the long reaction time of 72 hours is problematical, despite the use of a several-fold excess of the alkylating agent methyl iodide.

The corresponding diquaternization of the trans isomer was reported by T. Okawara, H. Takaishi, Y. Okamoto, T. Yamasaki and M. Furukawa in Heterocycles 41 (1995), 1023–1033. After treatment of trans-perhydro3a,5a,8a,10a-tetraazapyrene with 10 equivalents of methyl iodide in chloroform as a solvent at 60° C. in a bomb tube for 12 hours, trans-3a,8a-dimethyl-5a,10a-diaza-3a,8a-diazoniaperhydropyrenium diiodide is obtained in a yield of 67%. Here too, the period of 12 hours necessary for the reaction is not satisfactory when using a five-fold excess of alkylating agent and a reaction temperature of 60° C.

A number of diquaternizations with benzyl bromide as an alkylating agent were investigated by G. Weisman, E. Wong, D. Hill, M. Rogers, D. Reed and J. Calabrese in Chem. Commun. 1996, 947–948. Accordingly, the reaction of cis-perhydro-3a,5a,8a,10a-tetraazaopyrene with excess benzyl bromide in acetonitrile at room temperature affords cis-3a,8a-dibenzyl-5a,10a-diaza-3a,8a-diazoniaperhydropyrenium dibromide in 78–99% yield after a reaction time of 3 to 21 days.

These known processes for the preparation of the desired quaternary polycyclic polyammonium salts having a basic structure of the general formula (1) have a number of disadvantages: the yields achievable are in some cases only 67%, toxic acetonitrile or chloroform is employed as a solvent, and, with regard to environmental protection, questionable organic bromine and iodine compounds are employed as alkylating agents. A large excess of these reagents is moreover used, which makes the isolation of the desired products difficult. Consistently long reaction times of 12 hours at 60° C. up to 21 days at room temperature are moreover necessary, so that these methods are unsuitable for the preparation of industrial amounts of these quaternary polycyclic polyammonium salts.

SUMMARY OF THE INVENTION

This invention is therefore additionally based on the object of finding a simple process for the synthesis of quaternary polycyclic polyammonium salts having a basic structure of the general formula (1). In addition, the process according to the invention should be suitable for the preparation of industrial amounts and should avoid solvents which are questionable from the toxicological point of view; the resulting products should moreover be obtained in high yield with minimum amounts of waste.

Surprisingly, it has been found that when not organic bromine or iodine compounds, but other substances suitable for the transfer of alkyl groups, in particular dialkyl sulfates and esters of organic sulfonic acids, are used as alkylating agents, extremely short reaction times are sufficient for the synthesis of quaternary polycyclic polyammonium salts having a basic structure of the general formula (1).

The invention relates to quaternary polycyclic polyammonium salts of the general formula (2)

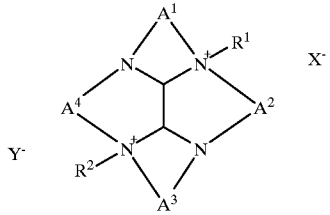

(2)

in which
A$^1$, A$^2$, A$^3$ and A$^4$ independently of one another are either
a C$_2$- to C$_4$-alkylene radical which can be substituted by one or more groups P and/or Q, where
P is a C$_1$- to a C$_{30}$-alkyl or cycloalkyl group which can be substituted by one or more groups Q, and
Q is a group COR, in which R is a hydroxyl group, a C$_1$- to C$_5$-alkoxy group or C$_6$- to C$_{14}$-aryloxy group or a substituted or unsubstituted amino group,
a C$_6$- to C$_{14}$-aryl group which can be substituted by one or more C$_1$- to C$_{30}$-alkyl, cycloalkyl or aryl groups, C$_1$- to C$_5$-alkoxy or C$_6$- to C$_{14}$-aryloxy groups, substituted or unsubstituted amino groups, halogen atoms, cyano groups, sulfo groups, carboxyl groups or
groups of the formula —(CH$_2$)$_r$—COOH, —(CH$_2$)$_r$—SO$_3$H, —(CH$_2$)$_r$—PO$_3$H$_2$, —(CH$_2$)$_r$OH, where r is an integer from 0 to 4 and the acid groups mentioned can also be present in salt form,
an aromatic heterocycle which contains nitrogen, oxygen and/or sulfur atoms and can be substituted by one or more C$_1$- to C$_{30}$-alkyl, cycloalkyl or aryl groups, C$_1$- to C$_5$-alkoxy groups or C$_6$- to C$_{14}$-aryloxy groups, substituted or unsubstituted amino groups, halogen atoms, cyano groups, sulfo groups, carboxyl groups or groups of the formula —(CH$_2$)$_r$—COOH, —(CH$_2$)$_r$—SO$_3$H, —(CH$_2$)$_r$—PO$_3$H$_2$, —(CH$_2$)$_r$OH, where r is an integer from 0 to 4 and the acid groups mentioned can also be present in salt form,
a substituted or unsubstituted amino group,
a hydroxyl group,
a C$_1$- to C$_{30}$-alkyl or cycloalkyl group,
a C$_1$- to C$_{30}$-alkoxy or C$_6$- to C$_{14}$-aryloxy group,
a halogen atom,
a cyano, sulfo or carboxyl group,
a group of the formula —(CH$_2$)$_r$—COOH, —(CH$_2$)$_r$—SO$_3$H, —(CH$_2$)$_r$—PO$_3$H$_2$, —(CH$_2$)$_r$OH, where r is an integer from 0 to 4 and the acid groups mentioned can also be present in salt form;
or A$^1$, A$^2$, A$^3$ and A$^4$ are a group —(CH$_2$)$_s$—E—(CH$_2$)$_t$—, in which E is a C$_6$- to C$_{14}$-arylene radical which can be substituted by groups P and/or Q, where the groups P and Q have the abovementioned meaning and s and t independently of one another can assume the values 0, 1 or 2, R$^1$ and R$^2$ independently of one another are a C$_1$- to C$_{16}$-alkyl, cycloalkyl or aryl group which can be substituted by one or more C$_1$- to C$_{20}$-alkyl, cycloalkyl or aryl radicals, C$_1$- to C$_4$-alkoxy groups, halogen atoms, sulfo groups, carboxyl groups or groups of the formula —(CH$_2$)$_w$—COOH, —(CH$_2$)$_w$—SO$_3$H, —(CH$_2$)$_w$—PO$_3$H$_2$, —(CH$_2$)$_w$—OH, where w is an integer from 0 to 5 and the acid groups mentioned can also be present in salt form, and
X$^-$ and Y$^-$ independently of one another are R$^3$SO$_4^-$ and SO$_4^{2-}$, where R$^3$ in each case is hydrogen, C$_1$- to C$_8$-alkyl, cycloalkyl or C$_6$- to C$_{18}$-aryl, optionally substituted by C$_1$- to C$_4$-alkyl.

DESCRIPTION OF THE PREFERRED EMBODIMENTS

Preferred compounds of the formula (2) are those in which A$^1$, A$^2$, A$^3$ and A$^4$ independently of one another are a C$_2$–C$_4$-alkylene radical, R$^1$ and R$^2$ independently of one another are a C$_1$–C$_{16}$-alkyl group, in particular a methyl group, or a cycloalkyl or aryl group and X$^-$ and Y$^-$ are CH$_3$SO$_4^-$, HSO$_4^-$ and/or SO$_4^{2-}$.

The term "C$_x$- to C$_y$-alkylene" is used to refer to substituted or unsubstituted alkyl carbon chains.

The invention additionally relates to a process for the preparation of the compounds of the formula (2), where A$^1$, A$^2$, A$^3$, A$^4$, R$^1$, R$^2$, X and Y have the abovementioned meanings and X and Y can additionally be F$^-$ or Cl$^-$. This process comprises reacting a polyamine of the formula (3)

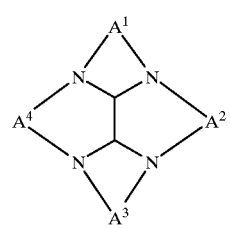

(3)

where A$^1$, A$^2$, A$^3$ and A$^4$ have the meanings indicated above, with a compound of the formula 4a or 4b R$^1$—Z (4a)

or

R$^2$—Z (4b)

where R$^1$ and R$^2$ have the meanings indicated above and Z has the same meaning as X and Y.

Examples of quaternary polycyclic polyammonium salts of the general formula 2 according to the invention are:
2a,6a-dimethyldecahydro-2a,4a,6a,8a-tetraazacyclopenta[f,g]acenaphthylene dimethylsulfate
2a,6a-dimethyldecahydro-2a,4a,6a,8a-tetraazacyclopenta[f,g]acenaphthylene sulfate
2a,7a-dimethyldecahydro-2a,4a,7a,9a-tetraazacyclopenta[c,d]phenalene dimethylsulfate
2a,7a-diethyldecahydro-2a,4a,7a,9a-tetraazacyclopenta[c,d]phenalene diethylsulfate
2a,7a-dibenzyldecahydro-2a,4a,7a,9a-tetraazacyclopenta[c,d]phenalene sulfate 3a,8a-dimethyldecahydro-3a,5a,8a,11a-
tetraazacyclohepta[d,e,f]phenanthrene dimethylsulfate 3a,8a-dicyclohexyldecahydro-3a,5a,8a,11a-
tetraazacyclohepta[d,e,f]phenanthrene sulfate 3a,8a-diphenyldecahydro-3a,5a,8a,11a-
tetraazacyclohepta[d,e,f,]phenanthrene sulfate 3a,8a-dimethyldecahydro-3a,5a,8a,10a-tetraazapyrene
dimethylsulfate 3a,8a-dimethyldecahydro-3a,5a,8a,10-tetraazapyrene sulfate 3a,8a-diethyldecahydro-3a,5a,8a,10a-tetraazapyrene
diethylsulfate 3a,8a-diethyldecahydro-3a,5a,8a,10a-tetraazapyrene sulfate 3a,8a-dibenzyldecahydro-3a,5a,8a,10a-tetraazapyrene
sulfate 3a,8a-diphenyldecahydro-3a,5a,8a,10a-tetraazapyrene
sulfate 3a,9a-dimethyldecahydro-3a,6a,9a,12a-tetraazadibenzo
[ef,k]heptalene dimethylsulfate 3a,9a-dibenzyldecahydro-3a,6a,9a,12a-tetraazadibenzo
[ef,k]heptalene sulfate 3a,9a-di(methoxymethyl)decahydro-3a,6a,9a,12a-
tetraazadibenzo[ef,k]heptalene sulfate, where in each case the cis and trans isomers and isomeric mixtures are intended. Biquaternary polycyclic polyammonium salts derived from decahydro-3a,5a,8a,10a-tetraazapyrene are particularly preferred.

The polycyclic polyamines of the formula 3 serving as starting substances for the process according to the invention can be prepared by condensation of glyoxal with cyclic tetraamines as described, for example, by G. Weisman, E. Wong, D. Hill, M. Rogers, D. Reed and J. Calabrese in Chem. Commun. 1996, 947–948. Examples of basic structures of polycyclic polyamines 3 of this type are cis- and trans-decahydro-2a,4a,6a,8a-tetraazacyclopenta
[f,g]acenaphthylene, cis- and trans-decahydro-2a,4a,7a,9a-tetraazacyclopenta
[c,d]phenalene, cis- and trans-decahydro-3a,5a,8a,10a-tetraazapyrene, cis- and trans-decahydro-3a,5a,8a,11a-tetraazacyclohepta
[def]phenanthrene or cis- and trans-decahydro-3a,6a,9a,12a-tetraazadibenzo
[ef,kl]heptalene.

In the case of the compounds of the formula 4a or 4b serving as starting substances for the process according to the invention, those compounds are employed which react with tertiary amines to give quaternary ammonium compounds. Examples of reactions or reagents 4a and 4b of this type are given in J. Goerdeler "Methoden zur Herstellung und Umwandlung von quartären Ammoniumverbindungen" [Methods for the Preparation and Conversion of Quaternary Ammonium Compounds], Methoden der Organischen Chemie [Methods of Organic Chemistry] (Houben-Weyl), E. M üller (Ed.), Vol. XI/2 (1958), pp. 587–640 and the references cited there. Preferred reagents 4a and 4b in this case are, in particular, esters of sulfuric acid and of the sulfonic acids such as, for example, dialkyl sulfates, aryl alkyl sulfates or esters of organic sulfonic acids such as, for example, methyl toluene- or methanesulfonates.

The reaction is customarily carried out in the presence of a solvent and it is also possible here to use the reagents 4a or 4b as a solvent. Solvents are preferred here which do not react with the compounds 3 or 4a and 4b under the conditions of the reaction; carboxylic acids or amines, for example, are therefore less suitable.

Customarily, an amount of solvent is employed for the reaction such that the compounds 3 and 4a or 4b dissolve therein. If complete dissolution should not take place, the reaction can also be carried out in a dispersion (suspension or emulsion). The concentration of compound of the formula 3 is customarily in the range from 0.01 to 5.0 mol per liter of solvent, preferably 0.05 to 3.5 mol/l, particularly preferably 0.1 to 2.0 mol/l.

The reaction is carried out at temperatures from 0 to 200° C., preferably 10 to 150° C. The period needed for this, depending on the temperature selected, is approximately 1 to 12 hours.

To carry out the process according to the invention, in general the compound 3, if appropriate introduced with the solvent, and then the reagent 4a or 4b is added, but it can also prove advantageous to introduce the compound 4a or 4b and, if appropriate, a solvent and to add the compound 3, if appropriate dissolved in a solvent; this is especially appropriate if the intermediately formed monoquaternary polycyclic polyammonium salt, i.e. the precursor of the diquaternary polycyclic polyammonium compound of the general formula (2), is only poorly soluble in the reaction medium used.

Since the reaction as a rule is of exothermic character, it may prove necessary to cool the reaction solution before, during and/or after the mixing together of 3 and 4a or 4b. Independently thereof, it may be necessary, however, to complete the reaction by warming after the mixing together of 3 and 4a or 4b.

After completion of the reaction, the quaternary polycyclic polyammonium salt of the general formula (2) formed is isolated from the reaction mixture using the customary processes. Suitable processes are, for example, filtration, extraction, distillative, chromatographic and osmotic processes, and combinations of these processes.

To avoid secondary reactions, the reaction and, if appropriate, the work-up can be carried out under protective gas, customarily nitrogen.

In the case of the compounds of the formula 2, those are preferred where the counterion is a sulfate, hydrogensulfate, alkyl- and arylsulfate or -sulfonate anion.

These compounds of the formula 2 surprisingly afford higher yields than the analogous halide salts in the reaction with sodium borohydride.

The process according to the invention, which also comprises the preparation of these halide salts, is distinguished by the production of small amounts of waste, very good yields and by starting substances which are easily accessible and in some cases also commercially accessible in large amounts.

EXAMPLE 1

Synthesis of cis-3a,8a-dimethyl-5a,10a-diaza-3a,8a-diazoniaperhydropyrenium dimethylsulfate 25.2 g of dimethyl sulfate were added dropwise with cooling to a solution of 11.1 g of cis-perhydro-3a,5a,8a,10a-tetraazapyrene in 160 ml of toluene. After stirring for two hours, 100 ml of water were added. The aqueous phase was separated off and washed three times with 50 ml of toluene, and the solvent was removed in vacuo. 23.7 g of colorless crystals were obtained.

$^1$H-NMR (D$_2$O, TMS): δ=1.92 (m, 2H), 2.4 (m, 2H), 2.7 (m, 2H), 3.08–3.32 (m, 8H)) 3.34 (s, 6H, CH$_3$), 3.65 (m, 4H), 3.76 (s, 6H, CH$_3$), 4.50 (m, 2H), 4.63 (s, 2H).

EXAMPLE 2

Synthesis of cis-3a,8a-dimethyl-5a-10a-diaza-3a,8a-diazoniaperhydropyrenium dimethylsulfate A solution of 49.3 g of dimethyl sulfate in 50 ml of acetonitrile was added dropwise in the course of 30 min to a solution of 44.5 g of cis-perhydro-3a,5a,8a,10a-tetraazapyrene in 500 ml of acetonitrile. After addition was complete, the reaction solution was stirred at room temperature for 2 hours. Removal of the solvent in vacuo afforded 90.4 g of a crystalline solid.

EXAMPLE 3

Synthesis of trans-3a,8a-dimethyl-5a,10a-diaza-3a,8a-diazonia-perhydropyrenium dimethylsulfate 18.9 g of dimethyl sulfate were added dropwise with cooling to a solution of 11.1 g of trans-perhydro-3a,5a,8a,10a-tetraazapyrene in 160 ml of ethanol, then the mixture was heated to boiling under reflux for two hours. The crystals deposited on cooling to room temperature were filtered off with suction and washed with 50 ml of ethanol. After drying in vacuo, 9.61 g of colorless crystals were obtained.

EXAMPLE 4

Synthesis of trans-3a,8a-dimethyl-5a,10a-diaza-3a,8a-diazonia-perhydropyrenium dimethylsulfate 200 ml of dimethyl sulfate were treated in portions with 44.5 g of trans-perhydro-3a,5a,8a,10a-tetraazapyrene in the course of 30 minutes and the mixture was stirred at room temperature for 8 hours. The precipitate deposited was filtered off with suction and dried in vacuo after washing with 100 ml of acetone. 43.5 g of a colorless, crystalline solid were obtained.

EXAMPLE 5

Synthesis of cis-3a,8a-dimethyl-5a,10a-diaza-3a,8a-diazonia-perhydropyrenium sulfate 3.7 g of dimethyl sulfate were added dropwise to a solution of 6.5 g of cis-decahydro 3a,5a,8a,10a-tetraazapyrene in 100 ml of xylene. The solution obtained was stirred under reflux for 4 days. The solvent was then removed in a high vacuum. The residual oil was recrystallized three times from isopropanol. 2.8 g of a white solid were obtained here.

EXAMPLE 6

Reaction of cis-3a,8a-dimethyl-5a,10a-diaza-3a,8a-diazonia-perhydropyrenium dimethylsulfate with sodium borohydride 4.75 g of cis-3a,8a-dimethyl-5a,10a-diaza-3a,8a-diazoniaperhydropyrenium dimethylsulfate were introduced into 30 ml of a mixture of ethanol/water (80:20). 2.25 g of sodium borohydride were added in portions to the solution, and the mixture was then stirred at room temperature for 48 hours. 2.85 g of hydrochloric acid (37%) were then added dropwise to the solution with ice-cooling, a white suspension resulting which was concentrated on a rotary evaporator to a volume of 10 ml. After cooling of the residue to 5° C., it was treated with 8 ml of a 10 M potassium hydroxide solution, extracted four times with toluene and the combined toluene phases were concentrated to dryness. 2.1 g (82%) of 4,11-dimethyl-1,4,8,11-tetraazabicyclo[6.6.2]hexadecane were obtained here in the form of a yellowish oil.

EXAMPLE 7

Reaction of cis-3a,8a-dimethyl-5a,10a-diaza-3a,8a-diazonia-perhydropyrenium diiodide with sodium borohydride (comparison experiment to Example 6)

7.2 g of sodium borohydride were added slowly with stirring to a heterogeneous mixture of 3.2 g of cis-3a,8a-dimethyl-5a,10a-diaza-3a,8a-diazoniaperhydropyrenium diiodide in 250 ml of ethanol. After stirring for 72 hours, the mixture was rendered slightly acidic with careful addition of 10% strength hydrochloric acid and diluted with 200 ml of ethanol. The solvent was removed on a rotary evaporator, the residue which remained was dissolved in 400 ml of water and a pH of 14 was established by addition of 40% strength potassium hydroxide solution. The alkaline solution was extracted four times with 300 ml of toluene in each case, the organic phases were dried over anhydrous sodium sulfate and the solvent was removed in vacuo. Distillation of the residue afforded 1.0 g (62%) of 4,11-dimethyl-1,4,8,11-tetraazobicyclo[6.6.2]hexadecane as a pale yellow oil.

What is claimed is:

1. A quaternary polyclic polyammonium salt of the formula (2)

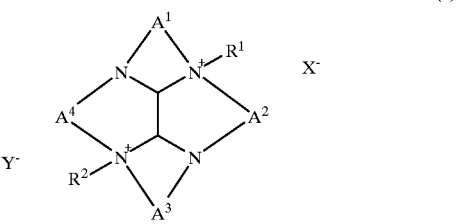

in which $A^1$, $A^2$, $A^3$ and $A^4$ independently of one another are either a $C_2$- to $C_4$-alkylene radical which can be substituted by one or more groups P, where P is a $C_1$- to a $C_{30}$-alkyl group or $A^1$, $A^2$, $A^3$ and $A^4$ are a group —$(CH_2)_s$—E—$(CH_2)_t$—, in which E is a $C_6$-arylene radical are 0,1 or 2, $R^1$ and $R^2$ independently of one another are a $C_1$- to $C_{16}$-alkyl group, and $X^-$ and $Y^-$ independently of one another are $R^3SO_4^-$ and $SO_4^{2-}$, where $R^3$ in each case is hydrogen, $C_1$- to $C_8$-alkyl, cycloalkyl or $C_6$- to $C_{18}$-aryl, optionally substituted by $C_1$- to $C_4$-alkyl.

2. A salt as claimed in claim 1, wherein $R^1$ and $R^2$ are both $C_1$- to $C_{16}$-alkyl groups.

3. A salt as claimed in claim 1, wherein $R^1$ and $R^2$ are both methyl groups.

4. A salt as claimed in claim 1, wherein $A^1$, $A^2$, $A^3$ and $A^4$ are the same or different and are selected from the group consisting of substituted or unsubstituted $C_2$- to $C_4$-alkyl groups, and aryl groups.

5. A salt as claimed in claim 1, wherein $A^1$ and $A^3$ are $C_3$-alkyl groups and $A^2$ and $A^4$ are $C_2$-alkyl groups.

6. A salt as claimed in claim 1, wherein $X^-$ and $Y^-$ are selected from the group consisting of $SO_4^{2-}$ and $R^3SO_4^-$, where R is hydrogen or $C_1$- to $C_8$ alkyl.

7. A salt as claimed in claim 1, wherein X⁻ and Y⁻ are selected from the group consisting of $CH_3$—$SO_4^-$, $HSO_4^-$ and $SO_4^{2-}$ ion.

8. A process for the preparation of compounds as claimed in claim 1, where $A^1$, $A^2$, $A^3$, $A^4$, $R^1$, $R^2$, X and Y have the meanings indicated in claim 1 which comprises reacting a polyamine of the formula (3)

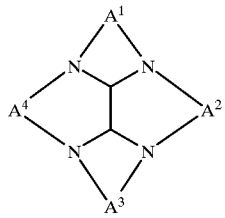

(3)

where A has the meanings indicated above for $A^1$, $A^2$, $A^3$ and $A^4$, with a compound of the formula 4a or 4b $R^1$—Z  (4a)

or $R^2$—Z  (4b)

where $R^1$ and $R^2$ have the meanings indicated above and Z has the same meaning as X and Y.

9. The process as claimed in claim 8, wherein at least one compound selected from the group consisting of $R^1$—$Z^1$ and $R^2$—$Z^2$ is present as a solvent.

10. The process as claimed in claim 8, wherein, per liter of solvent, 0.01 to 5.0 mol of the polyamine is employed.

11. The process as claimed in claim 8, wherein the reaction is carried out at a temperature from 0 to 200° C.

12. A quarternary polycyclic polyammonium salt of the formula

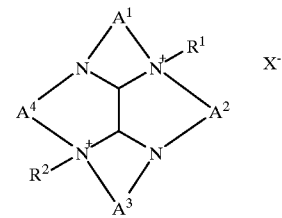

(2)

which:

$A^2$ and $A^4$ are the same or different and are selected from the group consisting of substituted or unsubstituted $C_2$–$C_{18}$ alkyl groups;

$A^1$ and are the same or different and are selected from the group consisting of substituted or unsubstituted $C_2$- to $C_4$-alkyl groups;

$R^1$ and $R^2$ are the same or different and are selected from the group consisting of $C_1$- to $C_{16}$-alkyl groups; and X⁻ and Y⁻ are differend and are selected from the group consisting of:
(a) $SO_4^{2-}$, and
(b) $R^3SO_4^-$, where $R^3$ is selected from the group consisting of:
(i) H,
(ii) $C_1$- to $C_8$-alkyl,
(iii) cycloalkyl, and
(iv) $C_6$- to $C_{18}$-aryl.

13. The process as claimed in claim 11, wherein the reaction is carried out at a temperature from 10° to 150° C.

* * * * *